United States Patent [19]

Maulding

[11] Patent Number: 4,482,745
[45] Date of Patent: Nov. 13, 1984

[54] PROCEDURE FOR PREPARING 1,3-DIPHENYL-1,3-PROPANEDIONE

[75] Inventor: Donald R. Maulding, Somerville, N.J.

[73] Assignee: American Cyanamid Company, Stamford, Conn.

[21] Appl. No.: 548,063

[22] Filed: Nov. 2, 1983

[51] Int. Cl.³ .............................................. C07C 45/45
[52] U.S. Cl. .................................................. 568/314
[58] Field of Search ................ 568/334, 396, 346, 314

[56] References Cited

U.S. PATENT DOCUMENTS

| 1,949,412 | 3/1934 | Dreyfus | 568/396 |
| 2,158,071 | 5/1939 | Hansley | 568/396 |
| 2,240,934 | 5/1941 | Krister | 568/396 |
| 3,326,933 | 6/1967 | Wright | 568/314 |
| 3,742,062 | 6/1973 | Chappelon et al. | 568/314 |

OTHER PUBLICATIONS

Magnani et al., Org. Syn. Coll., vol. III, p. 251.
Levine et al., J.A.C.S., vol. 67, pp. 1510–1515 (1945).
Anselme, J. Org. Chem., vol. 32, pp. 3716–3722 (1967).

*Primary Examiner*—James H. Reamer
*Attorney, Agent, or Firm*—H. G. Jackson

[57] ABSTRACT

The present invention provides a novel method for the preparation of 1,3-diphenyl-1,3-propanedione.

2 Claims, No Drawings

PROCEDURE FOR PREPARING 1,3-DIPHENYL-1,3-PROPANEDIONE

The invention is a novel method for the preparation of 1,3-diphenyl-1,3-propanedione, comprising reacting acetophenone with from 5 to 10 molar equivalents of methyl benzoate in the presence of from 1 to 2 molar equivalents of calcium oxide, in a temperature range of from 150° to 200° C. for from three to six hours under an inert nitrogen atmosphere while continuously removing the methyl alcohol which is formed during the reaction.

Known procedures for the condensation of acetophenone with methyl or ethyl benzoate giving 1,3-diphenyl-1,3-propanedione in 62 to 85% yields require the use of strong bases such as sodium ethoxide (A. Magnani and S. McElvain, *Org. Syn. Coll.* Vol. III, 251); sodium amide [R. Levine et al., *J. Am. Chem. Soc.*, 67, 1510 (1945)], or sodium hydride [J. P. Anselme, *J. Org. Chem.*, 32, 3716 (1967)]. However, many difficulties are encountered in handling large quantities of the above-mentioned bases, making their use undesirable and costly for large scale industrial production.

The object of the present invention is to provide a novel and useful method for the preparation of 1,3-diphenyl-1,3-propanedione comprising reacting acetophenone with methyl benzoate in the presence of calcium oxide.

The method of the present invention is graphically illustrated below:

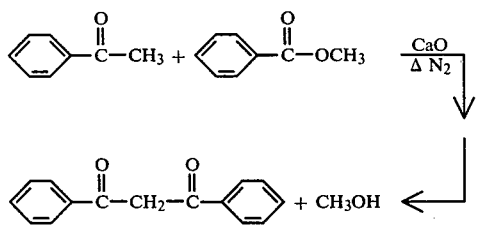

Thus, a mixture containing 1 mole of acetophenone and from 5 to 10 moles of methyl benzoate and from 1 to 2 moles of calcium oxide under an inert nitrogen atmosphere is heated at from 150° to 200° C. for from three to six hours while continuously removing by distillation the methyl alcohol which is formed during the reaction. The reaction mixture is then cooled, and an organic solvent such as toluene or xylene is added. The resulting mixture is acidified with hydrochloric acid, the organic layer separated and washed with aqueous sodium carbonate, and then with water to give a solution containing 1,3-diphenyl-1,3-propanedione. The product may be isolated by removing the solvent by distillation.

By the above procedure, 1,3-diphenyl-1,3-propanedione may readily be prepared in yields as high as 89%.

The process of this invention is of particular importance in the manufacture of 2-methyl-3,5-diphenylpyrazole and the conversion thereof to 1,2-dimethyl-3,5-diphenylpyrazolium methyl sulfate. The latter compound is a highly effective herbicidal agent. Moreover, said compound is especially useful since it is selective for the control of wild oats in the presence of a wide variety of small grains, such as barley, rape, wheat, and rye.

The herbicidal 1,2-dimethyl-3,5-diphenylpyrazolium methyl sulfate may be prepared by condensing 1,3-diphenyl-1,3-propanedione with methylhydrazine to form 2-methyl-3,5-diphenylpyrazole, which is then methylated with dimethyl sulfate as described in U.S. Pat. No. 3,882,142, and illustrated in Flow Diagram I below:

FLOW DIAGRAM I

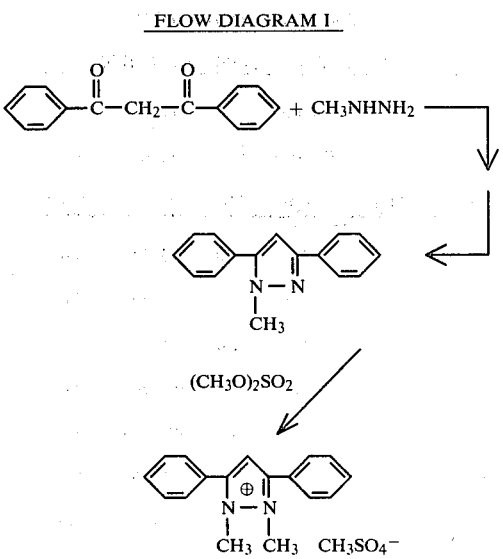

The present invention is further illustrated by the following non-limiting examples.

EXAMPLE 1

Preparation of 1,3-diphenyl-1,3-propanedione

A mixture containing 6.0 g (0.05 mol) of acetophenone, 40.8 g (0.30 mol) of methyl benzoate, and 3.73 g (0.06 mol) of 90% CaO is heated with stirring at 195°-200° C. for three and one-half hours while under nitrogen. The methanol (3.6 mL) that is distilled during the reaction is collected in a Dean Stark collector. The mixture is cooled, and 100 mL of toluene is added. The resulting mixture is cooled in cold water and acidified with 6N HCl. Stirring is continued until all of the solid is dissolved (ca 30 minutes). The toluene layer is separated and washed with aqueous $Na_2CO_3$ and water. Evaporation of the toluene solution gave 10 g of 1,3-diphenyl-1,3-propanedione as an oil representing an 89% yield based on acetophenone.

EXAMPLES 2-10

Effect of stoichiometry and temperature on the formation of 1,3-diphenyl-1,3-propanedione.

An investigation of the importance of stoichiometry of the reagents and the reaction temperature utilizing the procedure of Example 1 was undertaken varying the quantities of methyl benzoate, calcium oxide, and the reaction temperature and time.

The results of these experiments are summarized in Table I below which demonstrate the preferred operating conditions of the method of the invention.

TABLE I

EFFECT OF STOICHIOMETRY AND TEMPERATURE ON THE FORMATION OF 1,3-DIPHENYL-1,3-PROPANEDIONE

| Example | Acetophenone Mol | Methyl Benzoate Mol | CaO Mol | Temperature (°C.) | Time (Hour) | Yield (%)[a] of 3 |
|---|---|---|---|---|---|---|
| 2 | 1 | 6.0 | 1.2 | 195-200 | 3.5 | 89 |

TABLE I-continued

EFFECT OF STOICHIOMETRY AND TEMPERATURE ON THE FORMATION OF 1,3-DIPHENYL-1,3-PROPANEDIONE

| Example | Acetophenone Mol | Methyl Benzoate Mol | CaO Mol | Temperature (°C.) | Time (Hour) | Yield (%)[a] of 3 |
|---|---|---|---|---|---|---|
| 3 | 1 | 6.0 | 1.0 | 195–200 | 4.0 | 77 |
| 4 | 1 | 6.0 | 1.8 | 195–200 | 3.0 | 86 |
| 5 | 1 | 6.0 | 2.0 | 195–200 | 7.0 | 73 |
| 6 | 1 | 10.0 | 2.0 | 195–200 | 4.0 | 83 |
| 7 | 1 | 1.2 | 1.2 | 195–200 | 4.0 | 32 |
| 8 | 1 | 6.0 | 1.8 | 155–160 | 6.5 | 77 |
| 9 | 1 | 6.0 | 1.2 | 125 | 16.0 | 0 |
| 10 | 1 | 6.0 | 0.5 | 195–200 | 3.5 | 40 |

[a]Determined colorimetrically. Based on acetophenone.

What is claimed is:

1. A method for the preparation of 1,3-diphenyl-1,3-propanedione comprising admixing a mixture containing acetophenone with from 5 to 10 molar equivalents of methyl benzoate in the presence of from 1 to 2 molar equivalents of calcium oxide in a temperature range of from 150° to 200° C. for from three to six hours under a nitrogen atmosphere while continuously removing methyl alcohol as it is formed.

2. A method according to claim 1 wherein 1 mole of acetophenone is reacted with 6 moles of methyl benzoate in the presence of 1.2 moles of calcium oxide in a temperature range of 195° to 200° C. for three and one-half hours.

* * * * *